United States Patent [19]

Blanc et al.

[11] Patent Number: 4,835,320
[45] Date of Patent: May 30, 1989

[54] PROCESS FOR THE PREPARATION OF GLYOXAL MONOACTALS

[75] Inventors: Alain Blanc, Paris; Farid Hamedi-Sangsari, Lyons; Francine J. Chastrette, Caluire, all of France

[73] Assignee: Societe Francaise Hoechst, Puteaux, France

[21] Appl. No.: 61,015

[22] Filed: Jun. 1, 1987

[30] Foreign Application Priority Data

Jun. 3, 1986 [FR] France ................. 86 07957
Apr. 29, 1987 [FR] France ................. 87 06106

[51] Int. Cl.[4] ............... C07C 41/00; C07C 41/48; C07C 43/02
[52] U.S. Cl. .................. 568/465; 568/458; 568/461; 568/485; 568/492; 568/600
[58] Field of Search .......... 568/462, 461, 465, 469.9, 568/485, 486, 458, 600

[56] References Cited

U.S. PATENT DOCUMENTS 2,116,016 5/1938 Fischer ..................... 568/461

FOREIGN PATENT DOCUMENTS 379799 12/1983 Austria ..................... 568/461
2515001 3/1938 Fed. Rep. of Germany ...... 568/461

OTHER PUBLICATIONS

Kliegman et al., "J. Org. Chem.", vol. 38(3) 1973, pp. 556–560.
J. Org. Chem, vol. 38, No. 3, 1973 (Glyoxal Derivaties. V Reaction of Alcohols with Glyoxal) Jonathan M. Kliegman and Robert K. Barnes.

Primary Examiner—Werren B. Lone
Attorney, Agent, or Firm—Browdy and Neimark

[57] ABSTRACT

This process for the preparation of products of general formula (I):

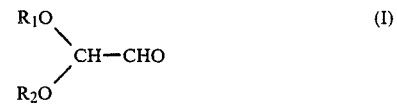

wherein either $R_1$ and $R_2$, which are identical, represent a —$CHRR_3$ group, in which R and $R_3$, which are identical or different, represent an alkyl, alkenyl or aralkyl group, or $R_1$ and $R_2$, which are identical, represent a —$CH_2R$ group, in which R represents a hydrogen atom, an alkyl, alkenyl or aralkyl radical, or $R_1$ and $R_2$ together form a —$CH_2$—$(CRR)_n$—CHR— radical, in which n represents 0 or 1 and R retains the meaning given previously, is characterized by reacting glyoxal in the presence of an acid catalyst with an excess of the corresponding alcohol of general formula (II) $RR_3CHOH$, (III) $RCH_2OH$ or (IV) —$(CRR)_n$—CHROH, in which R, $R_3$ and n retain the meaning given previously, then stopping the reaction as soon as the concentration of the desired monoacetal of general formula (I) decreases in the reaction medium in favor of bisacetal.

Application to the preparation of the novel product: 2,2-diallyloxy ethanal.

7 Claims, No Drawings

PROCESS FOR THE PREPARATION OF GLYOXAL MONOACTALS

BACKGROUND OF THE INVENTION

The present invention relates to a process for the preparation of monoacetalized glyoxal

1. Field of the Invention

The present invention relates to a process for the preparation of monoacetalized glyoxal of the general formula I:

wherein either $R_1$ and $R_2$, which are identical, represent a —$CHRR_3$ group, in which R and $R_3$, which are identical or different, represent an alkyl, alkenyl or aralkyl group, or $R_1$ and $R_2$, which are identical, represent a —$CH_2R$ group, in which R represents a hydrogen atom, an alkyl, alkenyl or aralkyl radical, or $R_1$ and $R_2$ together form a —$CH_2$—$(CRR)_n$—CHR— radical, in which n represents 0 or 1 and R retains the meaning given previously.

As examples of the —$CH_2$—$(CRR)_n$—CHR— radical it is possible to mention the ethylene, propylene, trimethylene, 2,2-dimethyl-propane-1,3-diyl groups, etc.

2. Description of the Prior Art

The reactions of glyoxal with alcohols have been studied extensively and they make it possible to have easy access to the corresponding glyoxal bisacetal (U.S. Pat. No. 2,194,405; GB Pat. No. 559.362; French Pat. Nos. 1.280.792 and 2.284.584; H. Fischer et al, Chem. Ber., 1926, 59, 851; D. H. Grangaard et al, J. Amer. Chem. Soc. 1939, 61, 428 and 755; M. Sprung et al, J. Amer. Chem. Soc., 1951, 73 1884; H. Fiesselmann et al, Chem. Ber., 1954, 87, 906; U. Faas et al, Chem. Ber. 1954, 87, 1343; J. M. Kliegman et al, J. Org. Chem., 1972, 37, 1276; ibid 1973, 38, 556; ibid 1974, 39, 1172; F. Chastrette et al, Bull. Soc. Chim. France, 1976, 601 and 613).

These direct methods have not made it possible to have access to glyoxal monoacetals, even though indirect methods have been used to obtain them, such as ozonolysis of the corresponding acetal of acrolein or the oxidizing cleavage of an α,β dihydroxylated acetal, such as 2,3-dihydroxy-1,1,4,4-tetraethoxy butane (C. Harries, Chem. Ber., 1903, 36, 1933; H. Fischer et al, Helv. Chim. Acta., 1939, 18, 514; L. Yanovkaya et al, Izvest. Akad. Nauk SSR, Otdel Khim. Nauk. 1963, 857; J. Hine et al, J. Amer. Chem. Soc., 1972, 94, 6998; P. Noire, Chemical Abstracts, 1978, 89, reference 215108).

These processes are long, difficult and sometimes even dangerous when they are applied to substantial amounts (cf. German Federal Republic Pat. No. 3.346.266).

SUMMARY OF THE INVENTION

The Applicants have now surprisingly discovered a novel process which with goods results provides rapid access to the products in formula I indicated above.

This process lies in reacting glyoxal in the presence of an acid catalyst with an excess of the corresponding alcohol of one of the general formulae (II) $RR_3CHOH$, (III) $RCH_2OH$ or (IV) $HOCH_2$—$(CRR)_n$—CHROH, in which R, $R_3$ and n retain the meaning given previously, then stopping the reaction as soon as the concentration of the desired monoacetal of general formula (I) decreases in the reaction medium in favour of bisacetal. In fact, the Applicants have observed that, even in an aqueous solution, glyoxal reacted rapidly with the alcohols of general formula (III) or (IV) so as to give the monoacetal of general formula (I), which was then transformed less rapidly into bisacetal.

Although the secondary alcohols of general formula (II) are much less reactive than the primary alcohols or biprimary or primary-secondary diols of general formula (III) or (IV), by increasing the reaction times it is possible to cause them to react, with satisfactory yield, with glyoxal so as to provide the desired monoacetal of the corresponding glyoxal.

This dissociation in the formation of glyoxal mono and bisacetal had never been foreseen, envisaged, reported or obtained in the numerous works devoted to the condensation of alcohols with glyoxal. However, the simplicity of the process according to the invention allows easy access not only to the previously described glyoxal monoacetals but also to new acetals, such as 2,2-diallyloxy ethanal which cannot be prepared using the known methods.

According to the process of the invention, the disappearance of glyoxal, on the one hand, and the formation of acetals, on the other hand, is followed by the analysis of samples taken regularly from the reaction medium.

The consumption of glyoxal is followed, for example, by determination of the soda required to transform it into sodium glycolate in accordance with Cannizzaro's reaction. With regard to the mono and bisacetals, they are preferably assayed by gas-phase chromatography after determination of the response coefficients using the conventional method of internal calibration.

Like all acetalization reactions, the process according to the invention is carried out in the presence of an acid catalyst. These acid catalysts include hydrogen chloride, sulphuric acid, paratoluenesulphonic acid, zirconium (IV) sulphate, ion-exchange sulphonic resins in acid form. Zirconium (IV) sulphate or ion-exchange sulphonic resins in acid form are preferably used. Normally, 50±25 mmoles of acid catalyst are used per mole of glyoxal introduced. At the end of the reaction, this acid catalyst is rapidly removed from the reaction medium by means known per se, for example by filtration, neutralization using a suitable base, etc.

The reaction is carried out with excess alcohol in relation to glyoxal. This excess may vary within substantial proportions but usually 12±5 moles of alcohol per mole of glyoxal are used. If necessary, it is possible to operate in an inert organic solvent which is compatible with this type of acid-catalyzed nucleophilic substitution reaction, such as hexane, cyclohexane, benzene, toluene, chlorinated solvents: chloroform, dichloromethane.

The starting glyoxal is either solid, such as its crystallized trimer with two molecules of water, or in aqueous solution. In this latter case, it is possible to eliminate part of the water of dissolution by prior azeotropic distillation.

As examples of the alcohols used in the process of the invention one may mention methanol, ethanol, propanol, 1-butanol, isobutyl alcohol, phenyl ethyl alcohol, allyl alcohol, ethylene glycol, 1,2-propanediol, 1,3-propanediol, 2,2-dimethyl-1,3-propanediol, etc.

Normally the reaction is carried out at the boiling point of the reaction medium but it can also be carried out at higher or lower temperatures. Normal operation takes place with azeotropic distillation of the water present and/or formed in the reaction medium with recycling of the dehydrated distillate by means known per se, such as leaching through a dessicating substance, such as anhydrous magnesium sulphate.

The reaction is generally carried out at atmospheric pressure, although a higher or lower pressure is not detrimental to the process.

At the end of the reaction, the desired glyoxal monoacetal is isolated from the reaction medium by means known per se, such a fractional distillation or crystallization.

The glyoxal monoacetals are very significant olefinoformylation "synthons" in organic synthesis and they are currently used to provide access, in particular, to certain heterocycles (D. Soerens et al, J. Org. Chem. 1979, 44, 535).

The following examples illustrate the invention but without implying any limitation thereof.

EXAMPLE 1

Preparation of 2,2-diethoxy ethanal

A mixture of:

81.7 g of glyoxal in aqueous solution at 71% by weight, i.e. 1 mole,
14.5 g (40 mmoles) of zirconium (IV) sulphate 98% crystallized with 4 moles of water,
400 g (8.7 moles) of ethanol, is heated for 90 minutes at boiling point.

The cooled reaction medium is then filtered (thereby enabling the majority of the catalyst used to be recovered), the filtrate is then treated with 10 g (12 mmoles) of dry sodium hydrogen carbonate. After filtration of the mineral salts and vacuum evaporation of the surplus ethanol, the oily residue obtained is treated with 5 volumes of diethyl oxide so as to eliminate the last traces of mineral salts. After filtration and vacuum evaporation of the diethyl oxide introduced, the residual oil is subjected to flash distillation under a vacuum of 10 mbar. 122 g of a liquid distilling at between 35° and 60° C. are thus collected, the vapour phase chromatographic analysis of which reveals the presence of about 70% of 2,2-diethoxy ethanal and 30% of 1,1,2,2-tetraethoxy ethane.

A second distillation carried out on a distillation apparatus with a rotating-belt column makes it possible to isolate 80 g (0.61 mole) of 2,2-diethoxy ethanal distilling at 43±2° C. at 11 mbar.

EXAMPLE 2

Preparation of 2,2-dibutoxy ethanal

A mixture of:

145 g (1 mole) of glyoxal in aqueous solution at 40% by weight,
740 g (10 moles) of 1-butanol,
100 g (100 g (100 meq.) of sulphonic resin in acid form, IMAC C16P, sold by the firm AKZO (cf. Kirk-Othmer, 3rd edition, volume 13, 696),
860 g of hexane, is heated for 5 hours at boiling point, the water present and formed in the reaction medium being eliminated by azeotropic distillation and the solvents being recycled.

At this stage, vapour phase chromatographic analysis of a sample of the reaction medium reveals the presence of 0.1 mole of unconverted glyoxal, 0.85 mole of 2,2-dibutoxy ethanal and 0.05 mole of 1,1,2,2-tetrabutoxy ethane.

The reaction medium is cooled, filtered and then the filtrate is treated with 50 g (0.6 mole) of sodium hydrogen carbonate. After filtration of the mineral salts and vacuum evaporation of the solvents, 250 g of clear yellow liquid are obtained, which is distilled under a vacuum of 2 mbar. The fraction distilling at 71±3° C. is collected. There are thus obtained 122 g of 2,2-dibutoxy ethanal, i.e. a yield of 65% calculated theoretically in relation to the glyoxal used. Upon continuing distillation, 9.6 g (30 mmoles) of 1,1,2,2-tetrabutoxy ethane distilling at 120±5° C. are collected, (Fiesselmann et al, Chem. Ber., 1954, 87, 911, $Eb_{10} = 160 \pm 1°$ C.).

Physical Analyses

NMR$^1$H (CDCl$_3$)

1 ppm (multiplet, 6H, CH$_3$)
1.4 ppm (multiplet, 8H, CH$_2$—CH$_2$)
3.6 ppm (multiplet, 4H, —CH$_2$—O)
4.55 ppm (doublet, 1H, J=2 Hz, >CH—C)
9.4. ppm (doublet, 1H, J=2 Hz, CHO).

As far as the Applicants are aware, this product has not been described in the prior art.

EXAMPLE 3

Preparation of 2,2-diallyloxy ethanal

A solution of:

1 mole of glyoxal in aqueous solution at 40% by weight,
50 mmoles of a catalyst C (or 50 acid meq. of a sulphonic resin),
10 mmoles of allyl alcohol;
1600 cm$^3$ of a solvent S giving an azeotrope with water, is heated to reflux for t hours with azeotropic distillation of the water and recycling of the organic solvent by means of a Dean-Stark apparatus.

When sampling of 2,2-diallyloxy ethanal and 1,1,2,2-tetraallyloxy ethane carried out at regular intervals during the heating indicates a decrease in the concentration of 2,2-diallyloxy ethanal in favour of 1,1,2,2-tetraallyloxy ethane, the reaction medium is cooled, then the catalyst is removed by filtration and/or by neutralization with an acid carbonate of an alkaline metal followed by filtration and then the reaction medium is distilled. After the solvents have been eliminated, there is collected a first fraction distilling at 62±2° C. at 6 mbar of p moles constituted by the desired product, then a second fraction distilling at 100±5° C. at 5 mbar of q moles constituted by 1,1,2,2-tetraallyloxy ethane.

The following Table I summarizes the tests carried out.

| Test No | t in hours | C catalyst | S solvent | p | q |
|---|---|---|---|---|---|
| 1 | 2 | H$_2$SO$_4$ conc. | benzene | 0.49 | 0.18 |
| 2 | 2 | Zr(SO$_4$)$_2$ | benzene | 0.51 | 0.27 |
| 3 | 5 | Resin A | benzene | 0.70 | 0.16 |
| 4 | 1.5 | Resin B | benzene | 0.54 | 0.29 |
| 5 | 5 | Zr(SO$_4$)$_2$ | chloroform | 0.53 | 0.12 |
| 6 | 10 | Resin A | chloroform | 0.70 | 0.13 |
| 7 | 6 | Resin B | chloroform | 0.57 | 0.23 |

Resin A: macroporous resin sold under the name IMAC C 16 P (cf. Encyclopedia of Chemical Technology, Kirk-Othmer, 3rd edition, 13, 696).

Resin B: NAFION resin (cf. Encyclopedia of Chemical Technology, Kirk-Othmer, 3rd edition S 559).

Physical Analyses

NMR$^1$H (CDCl$_3$)
4.2 ppm (doublet, 4H, OCH$_2$)
4.7 ppm (doublet, 1H, J=2 Hz, >CH—C)
5.2 ppm (multiplet, 4H, CH$_2$)
5.8 ppm (multiplet, 2H, =CH—)
9.5 ppm (doublet, 1H, J=2 Hz, CHO)

As far as the Applicants are aware, this product has not been described in the prior art.

EXAMPLE 4

Preparation of 2,2-dimethoxy ethanal

A mixture of:
81.7 g of glyoxal in aqueous solution at 71% by weight, i.e. 1 mole,
14.5 g of zirconium (IV) sulphate,
400 g (12.5 moles) of methanol,
is heated for 200 minutes at boiling point.

The reaction medium is then treated as in Example 1. There are thus obtained 73 g (0.7 mole) of 2,2-dimethoxy ethanal distilling at 40 mbar at 59±3° C. (L. A. Yanovskaya et al, Izvest. Akad. Nauk SSR, Otdel. Khim. Nauk. 1963, 857; Eb$_{39}$=59±1° C.) and 30 g (0.2 mole) of 1,1,2,2-tetramethoxy ethane distilling at 12 mbar at 53±2° C.

EXAMPLE 5

A mixture of:
70 g of commercial crystallized glyoxal (trimer crystallized with 2 moles of water, F=140–150° C.), i.e. 1 mole of glyoxal monomer,
14.5 g (40 mmoles) of zirconium sulphate 98% crystallized with 4 moles of water,
740 g (10 moles) of 2-methyl 1-propanol,
is heated for 4 hours at boiling point and the reaction medium is then treated as in Example 1. 113 g (0.6 mole) of 2,2-diisobutoxy ethanal are thus isolated, distilling at 52° C. at 6 mbar and 95 g (0.3 mole) of 1,1,2,2-tetraisobutoxy ethane distilling at 94°–99° C. at 5 mbar.

Physical Analyses

NMR$^1$H (CDCl$_3$)
0.94 ppm (doublet, 12H, CH$_3$)
1.9 ppm (multiplet, 2H, CH)
3.4 ppm (multiplet, 4H, CH$_2$O)
4.5 ppm (doublet, 1H, J=2 Hz)
9.5 ppm (doublet, 1H, J=2 Hz, CHO)

EXAMPLE 6

Preparation of 2-formyl 5,5-dimethyl 1,3-dioxane

A solution of:
145 g (1 mole) of glyoxal in aqueous solution at 35 to 40%,
104 g (1 mole) of 2,2-dimethyl 1,3-propanediol,
3.8 g (0.02 mole) of paratoluenesulphonic acid,
440 g of benzene,
is heated for 4 hours at boiling point, with azeotropic distillation of the water present and formed in the reaction medium, and with recycling of the solvents.

The reaction medium is then treated as in Example 2. 72.2 g (0.5 mole) of 2-formyl 5,5-dimethyl 1,3-dioxane are thus collected, distilling at 81±2° C. at 30 mbar.

Physical Analyses

NMR$^1$H (CDCl$_3$)
0.6 ppm (singlet, 3H, CH$_3$)
1 ppm (singlet, 3H, CH$_3$)
3.5 ppm (multiplet, 4H, CH$_2$)
4.5 ppm (doublet, 1H, J=52 Hz, CH)
9.3 ppm (doublet, 1H, J=2 Hz, CHO)

EXAMPLE 7

Preparation of 2,2-diisopropoxy ethanal

A solution formed by:
76 g of glyoxal in aqueous solution at 76.31% by weight, i.e. 1 mole,
420.7 g of 2-propanol, i.e. 7 moles,
19 g (0.1 mole) of paratoluenesulphonic acid crystallized with one mole of water,
is heated for 8 hours at boiling point and then, after cooling the reaction solution, the paratoluenesulphonic acid present is neutralized with sodium bicarbonate; the mineral salts are then filtered and unconverted isopropyl alcohol is removed under vacuum. The residual oil is then distilled under vacuum. The 2,2-diisopropoxy ethanal is thus isolated, distilling under a vacuum of 1 mbar at 32±3° C.

At ambient temperature, 2,2-diisopropoxy ethanal is a colourless, very fluid liquid which is soluble in water and the usual organic solvents.

Physical Analyses

NMR$^1$H (CDCl$_3$) at 200 MHz
9.36 ppm (d, 1H, J=2.9 Hz, CHO)
4.61 ppm (d, 1H, J=2.9 Hz, CH)
3.94 ppm (heptuplets, 2H, CH(Me)$_2$ J=6 Hz)
1.27 ppm (d, 6H, Me, J=6 Hz)
1.20 ppm (d, 6H, Me, J=6 Hz)

It is to be understood that the present invention has only been described by way of example and without limitation, and that any modification, particularly insofar as equivalents are concerned, could be made thereto without departing from the scope thereof.

What is claimed is:

1. A process for the preparation of products of formula I

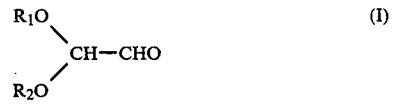

wherein either R$_1$ and R$_2$, which are identical, represent a —CH$_2$R group, in which R represents an hydrogen atom, an alkyl, alkenyl or aralkyl radical, or R$_1$ and R$_2$, which are identical, represent a —CHRR$_3$ group in which R has the above meaning and R$_3$ represents an alkyl group or R$_1$ and R$_2$ together form a —CH$_2$—(CRR)$_n$—CHR— radical, in which n represents 0 or 1 and R has the above meaning, comprising reacting glyoxal in the presence of an acid catalyst with an excess of the corresponding alcohol of formula (II) RR$_3$CHOH, (III) RCH$_2$OH or (IV) HOCH$_2$—(CRR)$_n$—CHROH, in which R, R$_3$ and n have the above meanings, then stopping the reaction as soon as the concentration of the desired monoacetal of formula (I) decreases in the reaction medium in favor of bisacetal by removal of the acid catalyst from the reaction medium and isolating the desired glyoxal monoacetal of formula (I) from the reaction medium.

2. A process as claimed in claim 1, in which the acid catalyst is an ion-exchange sulphonic resin in acid form.

3. A process as claimed in claim 1, in which the alcohol of general formula (II) $RR_3CHOH$ is 2-propanol.

4. A process as claimed in claim 1, in which the alcohol of general formula (III) $RCH_2OH$ is allyl alcohol.

5. A process as claimed in claim 1, in which the alcohol of general formula (III) $RCH_2OH$ is methanol.

6. A process as claimed in claim 1, in which the alcohol of general formula (III) $RCH_2OH$ is 1-butanol.

7. A process according to claim 1, comprising reacting one mole of glyoxal with 7 to 17 moles of the alcohol corresponding to said formula (II), (III) or (IV) in the presence of 25 to 75 mmoles of an acidic catalyst selected from the group consisting of hydrogen chloride, sulfuric acid, paratoluenesulfonic acid, zirconium sulfate and ion-exchange sulfonic resins in acid form, at boiling temperature of a solvent selected from the group consisting of hexane, cyclohexane, benzene, toluene, chloroform and dichloromethane, then cooling the reaction medium and neutralizing said acidic catalyst as soon as the concentration of the desired monoacetal of formula (I) decreases in said reaction medium in favor of bisacetal and then isolating from said medium said desired monoacetal of formula (I).

8. Novel 2,2-diallyloxy ethanal prepared using the process as claimed in claim 1.

* * * * *